(12) United States Patent
Kim et al.

(10) Patent No.: US 9,770,208 B2
(45) Date of Patent: Sep. 26, 2017

(54) PHOTOACOUSTIC PROBE AND PHOTOACOUSTIC DIAGNOSTIC APPARATUS

(71) Applicants: SAMSUNG MEDISON CO., LTD., Hongcheon-gun, Gangwon-do (KR); SAMSUNG ELECTRONICS CO., LTD., Suwon-si, Gyeonggi-do (KR)

(72) Inventors: Jung-ho Kim, Seoul (KR); Jong-kyu Jung, Seoul (KR); Dal-kwon Koh, Suwon-si (KR); Jung-taek Oh, Seoul (KR)

(73) Assignees: SAMSUNG MEDISON CO., LTD., Hongcheon-Gun, Gangwon-Do (KR); SAMSUNG ELECTRONICS CO., LTD., Suwon-si, Gyeonggi-Do (KR)

( * ) Notice: Subject to any disclaimer, the term of this patent is extended or adjusted under 35 U.S.C. 154(b) by 431 days.

(21) Appl. No.: 14/444,532

(22) Filed: Jul. 28, 2014

(65) Prior Publication Data
US 2015/0182167 A1 Jul. 2, 2015

(30) Foreign Application Priority Data
Dec. 30, 2013 (KR) .......................... 10-2013-0167490

(51) Int. Cl.
*A61B 8/00* (2006.01)
*A61B 5/00* (2006.01)

(52) U.S. Cl.
CPC .......... *A61B 5/6843* (2013.01); *A61B 5/0095* (2013.01); *A61B 5/6844* (2013.01); *A61B 5/7475* (2013.01); *A61B 8/429* (2013.01); *A61B 8/467* (2013.01); *A61B 2560/0266* (2013.01)

(58) Field of Classification Search
None
See application file for complete search history.

(56) References Cited

U.S. PATENT DOCUMENTS 6,171,303 B1 * 1/2001 Ben-Haim ........... A61B 5/0215 606/15
6,734,689 B1 5/2004 Yang
9,486,165 B2 11/2016 Choi et al.
(Continued)

FOREIGN PATENT DOCUMENTS

JP 2007-536053 A 12/2007
JP 2012-205886 A 10/2012
(Continued)

OTHER PUBLICATIONS

International Search Report issued in corresponding International Patent Application No. PCT/KR2014/006964 dated Nov. 6, 2014.
(Continued)

*Primary Examiner* — Jonathan Cwern
(74) *Attorney, Agent, or Firm* — McDermott Will & Emery LLP

(57) ABSTRACT

A photoacoustic diagnostic apparatus is provided. The photoacoustic diagnostic apparatus includes a movement restriction unit that selectively restricts a location movement of a user input unit that receives an input signal from a user for a light irradiation unit to irradiate light, based on a location of a contact detection unit that detects whether a probe contacts a subject to be imaged.

14 Claims, 11 Drawing Sheets

(56) References Cited

U.S. PATENT DOCUMENTS

| | | |
|---|---|---|
| 2003/0112220 A1 | 6/2003 | Yang et al. |
| 2006/0224123 A1* | 10/2006 | Friedli .............. A61M 5/31525 604/207 |
| 2007/0015978 A1 | 1/2007 | Kanayama et al. |
| 2007/0135767 A1* | 6/2007 | Gillespie, III ...... A61M 5/2033 604/135 |
| 2007/0255359 A1 | 11/2007 | Neev |
| 2008/0048128 A1* | 2/2008 | Braumandl .......... G01N 21/645 250/458.1 |
| 2008/0249380 A1 | 10/2008 | Van Beek et al. |
| 2011/0105867 A1 | 5/2011 | Schultz et al. |
| 2013/0168532 A1 | 7/2013 | Schmid et al. |
| 2013/0190591 A1 | 7/2013 | Hirson et al. |
| 2013/0338501 A1* | 12/2013 | Clingman ............. A61B 5/0035 600/440 |
| 2014/0005556 A1* | 1/2014 | Hirota .................. A61B 5/0095 600/476 |
| 2014/0018661 A1 | 1/2014 | Tsujita et al. |
| 2014/0049190 A1* | 2/2014 | Oh ..................... H05B 37/0227 315/307 |
| 2014/0051971 A1 | 2/2014 | Tokita |
| 2014/0296743 A1* | 10/2014 | Choi ................ A61B 5/150022 600/573 |
| 2015/0038955 A1* | 2/2015 | Bragagna ............. A61B 5/6843 606/12 |

FOREIGN PATENT DOCUMENTS

| | | |
|---|---|---|
| JP | 2012-231978 A | 11/2012 |
| WO | 2012/133975 A1 | 10/2012 |
| WO | 2012/150721 A1 | 11/2012 |

OTHER PUBLICATIONS

European Search Report issued in corresponding International Patent Application No. PCT/KR2014/006964 dated Jun. 30, 2017.

* cited by examiner

PHOTOACOUSTIC PROBE AND PHOTOACOUSTIC DIAGNOSTIC APPARATUS

RELATED APPLICATION

This application claims the benefit of Korean Patent Application No. 10-2013-0167490, filed on Dec. 30, 2013, in the Korean Intellectual Property Office, the disclosure of which is incorporated herein in its entirety by reference.

BACKGROUND

1. Field

One or more embodiments of the present invention relate to a photoacoustic probe used for a photoacoustic image diagnosis, and a photoacoustic diagnostic apparatus.

2. Description of the Related Art

Photoacoustic imaging technology is a technology for imaging biological tissues in a noninvasive way by using photoacoustic effects. If a short electromagnetic pulse of laser is incident on biological tissues, a portion of the energy is absorbed in the tissues and converted into heat, thereby generating a transient thermo-elastic expansion. As a result, ultrasound waves having frequencies of a wide range are released, and the ultrasound waves may be detected in various directions by a transducer for ultrasound waves to be converted into an image.

Since photoacoustic imaging is based on the conversion of optical energy into ultrasound waves for detection, this method has advantages of combining properties of optical imaging with those of ultrasound imaging. A pure optical imaging technology has a much higher contrast ratio than the ultrasound imaging technology. However, the pure optical imaging technology may form an image of biological tissues by only a predetermined depth from a surface of the biological tissues because of a high optical scattering in soft tissues. Compared to this, the ultrasound imaging technology has a high spatial resolution that enables a fetus inspection. The photoacoustic imaging technology is able to achieve both a high optical contrast and a high spatial resolution by overcoming a shallow imaging depth, which is the shortfall of the optical imaging, by an ultrasound conversion by photoacoustic effects.

There has been a significant progress in research for the photoacoustic imaging technology with respect to cancer, brains, hearts, and eyeballs of small animals. A photoacoustic imaging system may be easily fused with a conventional ultrasound imaging system, by only making a small revision (for example, a removal of an ultrasound transmission). Such an integrated system shares an acoustic detector, and thus, advantages of a traditional ultrasound imaging system such as portability and real-time imaging may be obtained in the integrated system.

However, for such a photoacoustic diagnostic apparatus, a laser of a short electromagnetic pulse is used, and, such a laser has a significant energy strength in general.

SUMMARY

One or more embodiments of the present invention include a photoacoustic probe and a photoacoustic diagnostic apparatus, in which a user input unit for light irradiation may be mechanically activated only when a user tries to use the photoacoustic diagnostic apparatus for obtaining a photoacoustic image.

Additional aspects will be set forth in part in the description which follows and, in part, will be apparent from the description, or may be learned by practice of the presented embodiments.

According to one or more embodiments of the present invention, a photoacoustic diagnostic apparatus includes: a photoacoustic probe including a light irradiation unit that irradiates light to a subject and a transducer that receives ultrasound generated from the subject, and converts them into electric signals; a contact detection unit that detects whether the photoacoustic probe contacts the subject and is capable of moving to a first location protruding outwards from the photoacoustic probe and to a second location inserted more inwards toward the photoacoustic probe than the first location; a user input unit that receives an input signal from a user for the light irradiation unit to irradiate light and is capable of moving to a third location in which the input signal is not received and to a fourth location in which the input signal is received; and a movement restriction unit that selectively restricts a location movement of the user input unit based on a location of the contact detection unit.

The user input unit may be restricted from moving from the third location to the fourth location when the contact detection unit is located in the first location.

The user input unit may move from the third location to the fourth location when the contact detection unit is located in the second location.

The movement restriction unit may include a first connection rod connected to the user input unit and a second connection rod connected to the contact detection unit and in which an insertion portion into which at least a portion of the first connection rod may be inserted is formed.

A movement direction of the first connection rod and a movement direction of the second connection rod may cross each other.

The first connection rod may be fixed to the user input unit.

The second connection rod may be fixed to the contact detection unit.

The photoacoustic diagnostic apparatus may further include a condition determination unit that is provided between the user input unit and the light irradiation unit and determines whether an image measurement mode is a photoacoustic image measurement mode to selectively connect between the user input unit and the light irradiation unit.

The movement restriction unit may further include a driving unit that moves the second connection rod.

The driving unit may selectively move the second connection rod based on the location of the contact detection unit.

The photoacoustic diagnostic apparatus may further include a condition determination unit that is provided between the driving unit and the contact detection unit and determines whether an image measurement mode is a photoacoustic image measurement mode to selectively connect the driving unit and the contact detection unit.

The user input unit may be formed in the photoacoustic probe.

According to one or more embodiments of the present invention, a photoacoustic probe includes: a probe body; a light irradiation unit that is disposed inside the probe body and irradiates light to a subject; a transducer that is disposed inside the probe body and receives ultrasound and converts them into an electric signal; a contact detection unit that detects whether the probe body contacts the subject and is capable of moving to a first location protruding outwards from the probe body and to a second location inserted more inwards toward the probe body than the first location; a user input unit that receives an input signal from a user for the light irradiation unit to irradiate light and is capable of moving to a third location in which the input signal is not received and to a fourth location in which the input signal is received; and a movement restriction unit that selectively restricts a location movement of the user input unit based on a location of the contact detection unit.

The user input unit may be restricted from moving from the third location to the fourth location when the contact detection unit is located in the first location.

The user input unit may move from the third location to the fourth location when the contact detection unit is located in the second location.

BRIEF DESCRIPTION OF THE DRAWINGS

These and/or other aspects will become apparent and more readily appreciated from the following description of the embodiments, taken in conjunction with the accompanying drawings in which.

DETAILED DESCRIPTION

Figure 1:
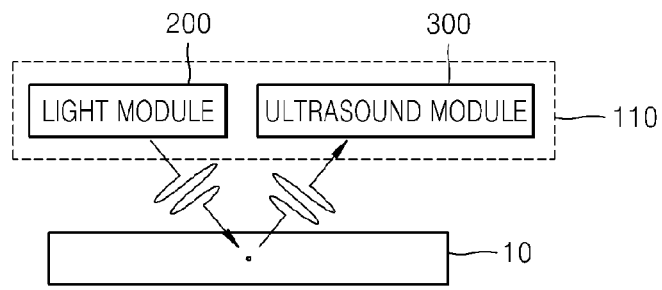
FIG. 1 is a block diagram schematically illustrating a photoacoustic probe.

The terms used in the present invention are selected from among common terms that are currently used in consideration of their function in the present invention. However, the terms may be different according to an intention of one of ordinary skill in the art, a precedent, or the advent of new technology. Also, in particular cases, the terms are discretionally selected by the applicant of the present invention, and the meaning of those terms will be described in detail in the corresponding part of the detailed description. Therefore, the terms used in the present invention are not merely designations of the terms, but the terms are defined based on the meaning of the terms and content throughout the present invention.

Throughout the present application, when a part "includes" an element, it is to be understood that the part additionally includes other elements rather than excluding other elements as long as there is no particular opposing recitation. Also, the terms such as " . . . unit", "module", or the like used in the present application indicate an unit, which processes at least one function or motion, and the unit may be implemented by hardware or software, or by a combination of hardware and software.

Throughout the specification, the term "image" indicates an image of a subject which is obtained by using a photoacoustic apparatus. The subject may include people or animals, or a part of people or animals. For example, the subject may include organs, such as a liver, heart, uterus, brain, breast, abdomen, or blood vessels. Also, the subject may include a phantom. A phantom may refer to a material having a volume that is very close to a density and effective atomic number of an organism.

Also, the image may include an ultrasound image and a photoacoustic image. The ultrasound image may be an image obtained by transmitting ultrasound waves to a subject and based on an echo signal reflected from the subject. The photoacoustic image may be an image obtained by irradiating light (for example, a laser) to a subject and based on a photoacoustic signal received from the subject.

Ultrasound images may be implemented in various ways. For example, an ultrasound image may be at least one of an amplitude mode (A mode), a brightness mode (B mode), a color mode (C mode), and a Doppler mode (D mode).

Also, according to an embodiment of the present invention, the image may be a 2-dimensional (2D) image or a 3-dimensional (3D) image.

Throughout this specification, the term "user" indicates a medical professional such as a doctor, a nurse, a medical technician, or a medical imaging technician, or indicates an engineer who repairs a medical apparatus, but it is not limited thereto.

Reference will now be made in detail to embodiments, examples of which are illustrated in the accompanying drawings, wherein like reference numerals refer to the like elements throughout. In this regard, the present embodiments may have different forms and should not be construed as being limited to the descriptions set forth herein. Accordingly, the embodiments are merely described below, by referring to the figures, to explain aspects of the present description. Expressions such as "at least one of," when preceding a list of elements, modify the entire list of elements and do not modify the individual elements of the list.

FIG. 1 is a block diagram schematically illustrating a photoacoustic probe 110. The photoacoustic probe 110 is a device that irradiates light to a subject 10 and receives ultrasound waves created as a result of photoacoustic effects. The photoacoustic probe 110 may include a light module 200 that irradiates light to the subject 10 and an ultrasound module 300 that receives ultrasound waves, and converts them into electric signals. The photoacoustic probe 110 may move along the subject 10 in a state contacting the subject 10, thereby irradiating light to the subject 10 and receiving ultrasound.

When manufacturing the photoacoustic probe 110, the light module 200 and the ultrasound module 300 may be integrally manufactured. However, it is not limited thereto. The light module 200 and the ultrasound module 300 may be separately manufactured to be later combined. Also, the light module 200 and the ultrasound module 300 are attachable and detachable. Thus, the ultrasound module 300 may individually operate for ultrasound imaging, or may operate for photoacoustic imaging when the light module 200 is attached. Alternatively, the ultrasound module 300 may operate for ultrasound imaging or photoacoustic imaging according to a user command, even in a condition that the light module 200 and the ultrasound module 300 are combined.

Laser light used in the photoacoustic probe 110 for the photoacoustic imaging may have specific wavelengths. For example, the light may include wavelengths of about 250 nm to about 1200 nm. Such a light is classified as a type highly dangerous for a human body, and may instantly become a cause of irretrievable accidents, such as blindness, burn injuries, and fires. Thus, lots of cautions are required in using the photoacoustic probe 110. For this, it is desirable that light should not be irradiated in the photoacoustic probe 110 at an unintended moment. In other words, it is desirable that the light should not be irradiated when a user manipulates a user input unit 230 (refer to FIGS. 2A and 2B) through his/her carelessness and the light should be irradiated only when certain conditions are met. According to the photoacoustic probe 110 according to an embodiment of the present invention, light may be irradiated by a light irradiation unit only under a certain condition.

Figure 2A:
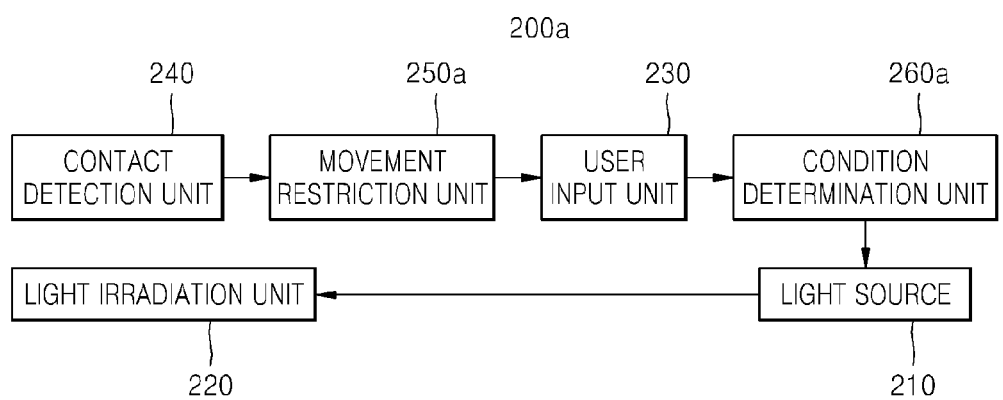
FIG. 2A is a block diagram of a light module according to an embodiment of the present invention.

FIG. 2A is a block diagram illustrating a light module 200*a* according to an embodiment of the present invention. As illustrated in FIG. 2A, the light module 200*a* may include a light source 210 that provides light for photoacoustic imaging, a light irradiation unit 220 that irradiates light to a subject 10, a user input unit 230 that receives an input signal from a user for the light source 210 to provide light, and a contact detection unit 240 that detects whether the light module 200*a* contacts the subject 10. A movement restriction unit 250*a* that selectively restricts a location movement of the user input unit 230 may be disposed between the contact detection unit 240 and the user input unit 230. A condition determination unit 260*a* that determines whether an image measurement mode satisfies a photoacoustic image measurement mode may be disposed between the user input unit 230 and the light source 210.

The light source 210 may provide light to induce ultrasound waves from the subject 10. The light source 210 may include a laser diode that generates a laser. The laser may be a pulse laser, and a pulse width of the laser may be a nano-unit size or a pico-unit size. Alternatively, the laser may be a continuous laser. Wavelength ranges of light provided by the light source 210 may be from about 250 nm to about 1200 nm, but not limited thereto. The light source 210 may provide light that has one central wavelength range, but may also provide lights with different wavelength ranges.

The light irradiation unit 220 may receive light from the light source 210 and irradiate the received light to the subject 10. The light irradiation unit 220 may receive the light from the light source 210 via an optical fiber (not shown). As the light is irradiated to the subject 10, a temperature of the subject 10 increases and a thermal expansion occurs in the subject 10, thereby generating ultrasound waves.

The contact detection unit 240 is to determine whether the photoacoustic probe 110 contacts the subject 10 or is in a state close to the subject 10 within a predetermined distance. The contact detection unit 240 is capable of a location movement by a contact with the subject 10. For example, the contact detection unit 240 protrudes over the photoacoustic probe 110 and may move backwards by the contact with the subject 10. When the contact detection unit 240 is pressurized by the subject 10, as the user makes the contact detection unit 240 contact the subject 10, the contact detection unit 240 moves in an opposite direction of the protruding direction. The contact detection unit 240 is capable of moving to a first location 240-1 (refer to FIG. 6A) protruding outwards from the photoacoustic probe 110, and, when contacting the subject 10, to a second location 240-2 (refer to FIG. 6B) that is more inside the photoacoustic probe 110 than the first location 240-1. Since the contact detection unit 240 has a structure in which the location of the contact detection unit moves by a physical contact with the subject 10, a malfunction that may be caused by a surrounding environment, for example, a temperature condition, may be prevented.

The user input unit 230 is connected to the light source 210 and receives an input signal from the user for the light irradiation unit 220 connected to the light source 210 to irradiate light. As the input signal received by the user input unit 230 is transmitted to the light source 210, the light source 210 may provide light for photoacoustic imaging to the light irradiation unit 220. The user input unit 230 may be a press button whereby an input signal is received by pressurization or depressurization by the user. For example, as the user moves the user input unit 230 from a third location 230-1 (refer to FIG. 6A) to a fourth location 230-2 (refer to FIG. 6B) by pressurizing the user input unit 230, the input signal may be received. The user input unit 230 is in a state in which the user input unit 230 does not receive the input signal, when the user input unit 230 is in the third location 230-1. The user input unit 230 is in a state in which the user input unit 230 receives the input signal, when the user input unit 230 is in the fourth location 230-2. The fourth location 230-2 may be a location further moved toward a direction of the pressurization than the third location 230-1. However, according to a design, the fourth location 230-2 may be a location further moved toward an opposite direction of the pressurization direction than the third location 230-1.

The movement restriction unit 250*a* that selectively restricts the movement of the user input unit 230 is disposed between the contact detection unit 240 and the user input unit 230. The movement restriction unit 250*a* mechanically activates or non-activates the user input unit 230 based on the location of the contact detection unit 240.

For example, when the contact detection unit 240 is located in the first location 240-1, the movement restriction unit 250*a* may restrict the location movement of the user input unit 230. That is, the movement restriction unit 250*a* may non-activate the user input unit 230. Thus, even if the user manipulates the user input unit 230 in a condition that the photoacoustic probe 110 is not close to the subject 10, the location movement of the user input unit 230 may be restricted. By this, light may be prevented from being unintentionally irradiated by the light irradiation unit 220, thereby effectively preventing damage to a human body due to the unintentional light irradiation.

When the contact detection unit 240 is located in the second location 240-2, the location movement of the user input unit 230 may be permitted. That is, the user input unit 230 may be activated. When the user pressurizes the user input unit 230 in a condition that the photoacoustic probe 110 is close to the subject 10, the user input unit 230 may move to the fourth location 230-2 so that light may be irradiated by the light irradiation unit 220.

A condition determination unit 260*a* may be disposed between the user input unit 230 and the light source 210. The condition determination unit 260*a* may selectively block an electrical connection between the user input unit 230 and the light source 210, based on an image measurement mode. In addition to a photoacoustic image measurement mode that measures a photoacoustic image, the image measurement mode may include various measurement modes, such as an ultrasound image measurement mode that measures an ultrasound image and a non-image measurement mode that does not measure an image. When the image measurement mode is the photoacoustic image measurement mode, the condition determination unit 260a transmits an input signal from the user input unit 230 to the light source 210. However, when the image measurement mode is not the photoacoustic image measurement mode, for example, when the image measurement mode is the ultrasound image measurement mode, the input signal from the user input unit 230 is not transmitted to the light source 210.

As shown above, the condition determination unit 260a does not transmit an input signal to the light source 210 unless the image measurement mode is the photoacoustic image measurement mode, even if the above described two conditions that the contact detection unit 240 is located in the second location 240-2 and the user input unit 230 is located in the fourth location 230-2 are met. Accordingly, light is not irradiated by the light irradiation unit 220. By this, irradiation of light which may be dangerous to a human body, due to carelessness of a user, may be more effectively prevented.

Figure 2B:
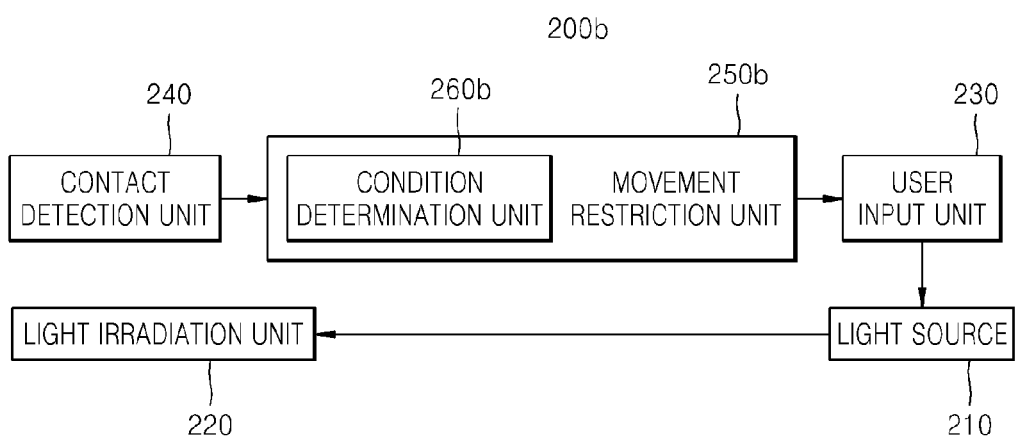
FIG. 2B is a block diagram of a light module according to another embodiment of the present invention.

FIG. 2B is a block diagram of a light module 200b according to another embodiment of the present invention. Compared to FIG. 2A, a condition determination unit 260b may be disposed between the contact detection unit 240 and the user input unit 230. For example, the condition determination unit 260b may be included in a movement restriction unit 250b.

The movement restriction unit 250b including the condition determination unit 260b restricts a location movement of the user input unit 230, when the contact detection unit 240 is located in the first location 240-1. The movement restriction unit 250b including the condition determination unit 260b restricts or permits the location movement of the user input unit 230 according to an image measurement mode, when the contact detection unit 240 is located in the second location 240-2. For example, the movement restriction unit 250b permits the location movement of the user input unit 230 when the image measurement mode is a photoacoustic image measurement mode, but restricts the location movement of the user input unit 230 when the image measurement mode is not the photoacoustic image measurement mode. Like this, when the image measurement mode is not the photoacoustic image measurement mode, the movement restriction unit 250b including the condition determination unit 260b restricts the location movement of the user input unit 230 even when the contact detection unit 240 is located in the second location 240-2, and thus, light irradiation due to carelessness of a user may be more stably prevented.

Although the light modules 200a and 200b necessarily include the light irradiation unit 220, at least some of the light source 210, the contact detection unit 240, the user input unit 230, and the condition determination units 260a and 260b may be included in other devices. For example, the light modules 200a and 200b may not include the light source 210. Also, the light modules 200a and 200b may not include the user input unit 230.

Figure 3:
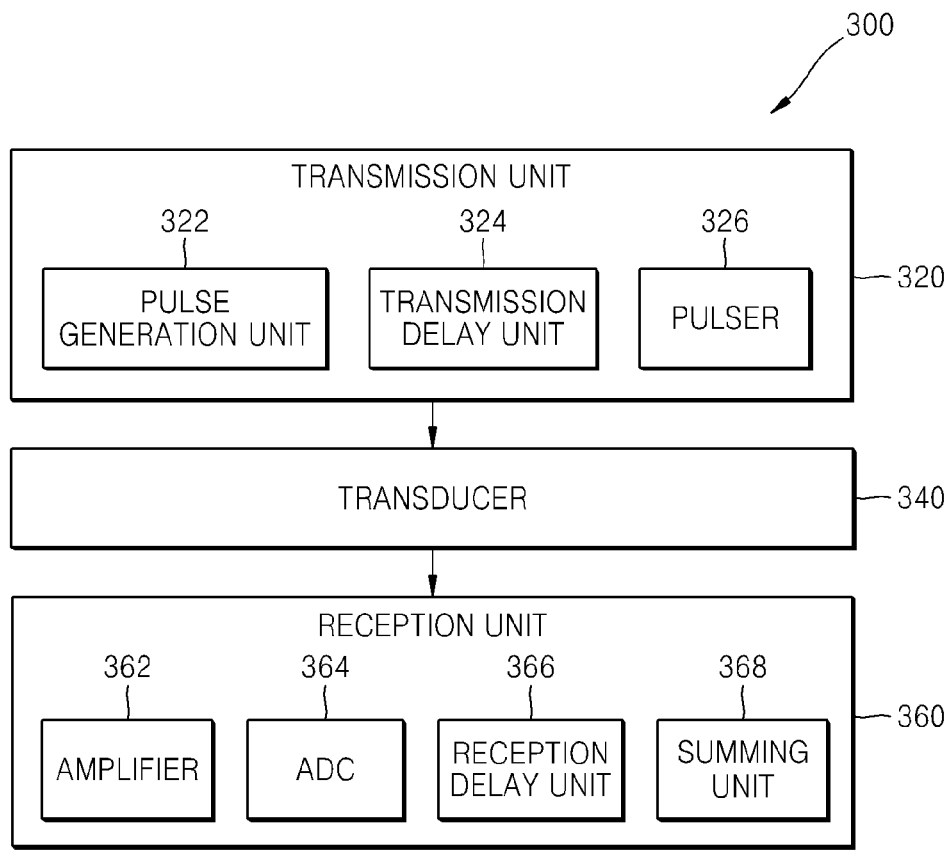
FIG. 3 is a block diagram of an ultrasound module according to an embodiment of the present invention.

FIG. 3 is a block diagram illustrating an ultrasound module 300 according to an embodiment of the present invention. Referring to FIG. 3, the ultrasound module 300 may include a transmission unit 320, a transducer 340, and a reception unit 360.

The transmission unit 320 supplies a driving signal to the transducer 340. The transmission unit 320 may include a pulse generation unit 322, a transmission delay unit 324, and a pulser 326.

The pulse generation unit 322 generates a rate pulse to form transmission ultrasound waves corresponding to a predetermined pulse repetition frequency (PRF). The transmission delay unit 324 applies a delay time to determine transmission directionality to the rate pulse generated by the pulse generation unit 322. Each rate pulse to which the delay time is applied corresponds to each of a plurality of unit devices included in the transducer 340. The pulser 326 applies a driving signal (or a driving pulse) to the transducer 340 by a timing corresponding to each rate pulse to which the delay time is applied. The plurality of unit devices may be in a shape of a one-dimensional array or a two-dimensional array.

The transducer 340 transmits ultrasound waves to the subject 10 according to the driving signal supplied from the transmission unit 320 and receives an echo signal of the ultrasound waves reflected from the subject 10. The transducer 340 may include a plurality of unit devices that convert an electric signal into acoustic energy (or vice versa). The plurality of unit devices may be in a shape of a one-dimensional array or a two-dimensional array.

The transducer 340 may be realized as a piezoelectric micromachined ultrasonic transducer (pMUT) that oscillates and interconverts ultrasound waves and electric signals by a change in pressure, a capacitive micromachined ultrasonic transducer (cMUT) that interconverts ultrasound waves and electric signals by a change in capacitance, a magnetic micromachined ultrasonic transducer (mMUT) that interconverts ultrasound waves and electric signals by a change in a magnetic field, and an optical ultrasonic detection that interconverts ultrasound waves and electric signals by a change in optical characteristics.

The reception unit 360 generates ultrasound data by processing signals received from the transducer 340. The reception unit 360 may include an amplifier 362, an analog to digital converter (ADC) 364, a reception delay unit 366, and a summing unit 368.

The amplifier 362 amplifies the signals received from the transducer 340, and the ADC 364 performs analog to digital conversion on the amplified signals. The reception delay unit 366 applies a delay time to determine reception directionality to the signals converted to the digital signals. The summing unit 368 generates ultrasound data by summing the signals processed by the reception delay unit 366. By the summing process of the summing unit 368, a reflection element from a direction determined by the reception directionality may be emphasized.

While the ultrasound module 300 necessarily includes the transducer 340, at least some of the components in the transmission unit 320 and the reception unit 360 may be included in another device. For example, the ultrasound module 300 may not include the summing unit 368 of the reception unit 360. In addition, the transmission unit 320 among components in the ultrasound module 300 may not operate when a photoacoustic image mode is selected, and, the ultrasound module 300 may not include the transmission unit 320 itself.

When ultrasound waves are generated from the subject 10 by photoacoustic effects, the transducer 340 receives the ultrasound waves generated from the subject 10, converts the received ultrasound waves into an electrical signal, and applies the converted signal to the reception unit 360. The reception unit 360 may generate image data from the electric signal and the image data generated by the reception unit 360 may be a basis of a photoacoustic image.

Figure 4:
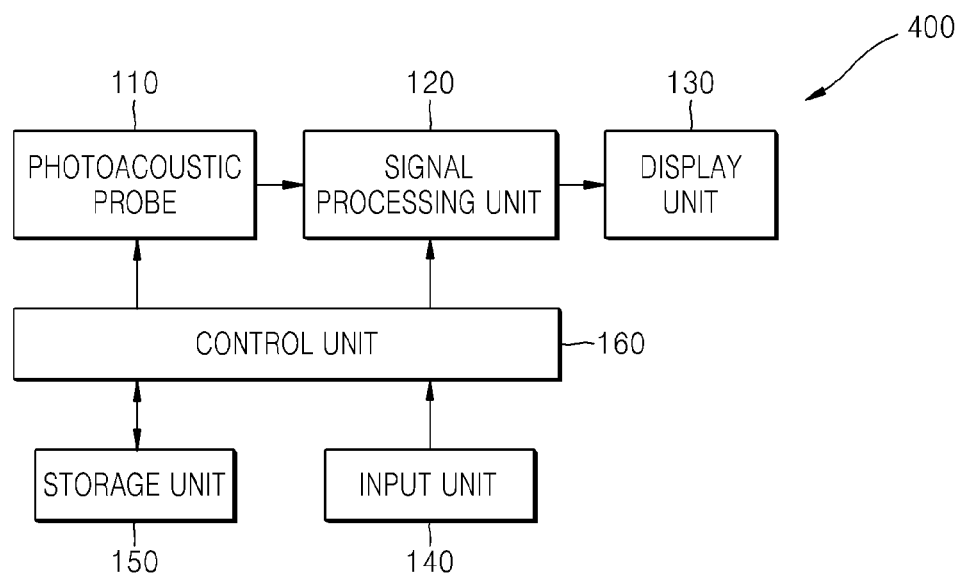
FIG. 4 is a block diagram of a photoacoustic diagnostic apparatus according to an embodiment of the present invention.

FIG. 4 is a block diagram illustrating a photoacoustic diagnostic apparatus 400 according to an embodiment of the present invention. Referring to FIG. 4, the photoacoustic diagnostic apparatus 400 includes the photoacoustic probe 110 that irradiates light to the subject 10 and receives ultrasound waves from the subject 10, a signal processing unit 120 that processes signals applied from the photoacoustic probe 110 to generate an image, a display unit 130 that displays the image, an input unit 140 that receives an input of a user command, a storage unit 150 that stores various information, and a control unit 160 that controls general operations of the photoacoustic diagnostic apparatus 400.

The photoacoustic probe 110 is a device that irradiates light to the subject 10 and receives ultrasound waves generated from the subject 10. Since the photoacoustic probe 110 is described above, their descriptions will not be made in detail herein.

The signal processing unit 120 may process ultrasound data obtained by the photoacoustic probe 110 to generate a photoacoustic image. Conventional method of generating the photoacoustic image may be used, and thus, its detailed descriptions will not be made herein. Also, the signal processing unit 120 may generate an ultrasound image. Conventional method of generating the ultrasound image may be used, and thus, its detailed descriptions will not be made herein.

The display unit 130 displays information processed in the photoacoustic diagnostic apparatus 400. For example, the display unit 130 may display the photoacoustic image generated by the signal processing unit 120 and may display a graphical user interface (GUI) window to request a user input.

The display unit 130 may include at least one of a liquid crystal display, a thin film transistor-liquid crystal display, an organic light-emitting diode, a flexible display, a three-dimensional (3D) display, and an electrophoretic display. The photoacoustic diagnostic apparatus 400 may include two or more display units 130 according to embodiments.

The input unit 140 denotes a means by which a user inputs data to control the photoacoustic diagnostic apparatus 400. The input unit 140 includes not only the user input unit 230 that receives an input signal from the user to irradiate light, but also a means to input data with respect to patient information and an image measurement mode. The input unit 140 may include various input means, such as a key pad, a mouse, a touch panel, a track ball, a jog wheel, and a jog switch.

The storage unit 150 stores various information processed in the photoacoustic diagnostic apparatus 400. For example, the storage unit 150 may store medical data related to a diagnosis of the subject 10, such as an image, and may store an algorithm or a program performed in the photoacoustic diagnostic apparatus 400.

The storage unit 150 may include at least one type of storage medium of a flash memory type, a hard disk type, a multimedia card micro type, card type memory (SD memory, XD memory), random access memory (RAM), static random access memory (SRAM), read-only memory (ROM), electrically erasable programmable read-only memory (EEPROM), programmable read-only memory (PROM), magnetic memory, a magnetic disk, and an optical disk. Also, the photoacoustic diagnostic apparatus 400 may run a web storage that performs a storage function of the storage unit 150 on the web or a cloud server.

The control unit 160 controls general operations of the photoacoustic diagnostic apparatus 400. That is, the control unit 160 may control operations of the photoacoustic probe 110, the signal processing unit 120, and the display unit 130. For example, the control unit 160 may control the signal processing unit 120 to generate an image by using a user command input via the input unit 140 or by using a program stored in the storage unit 150. Also, the control unit 160 may control the display unit 130 to display the image generated by the signal processing unit 120.

Figure 5:
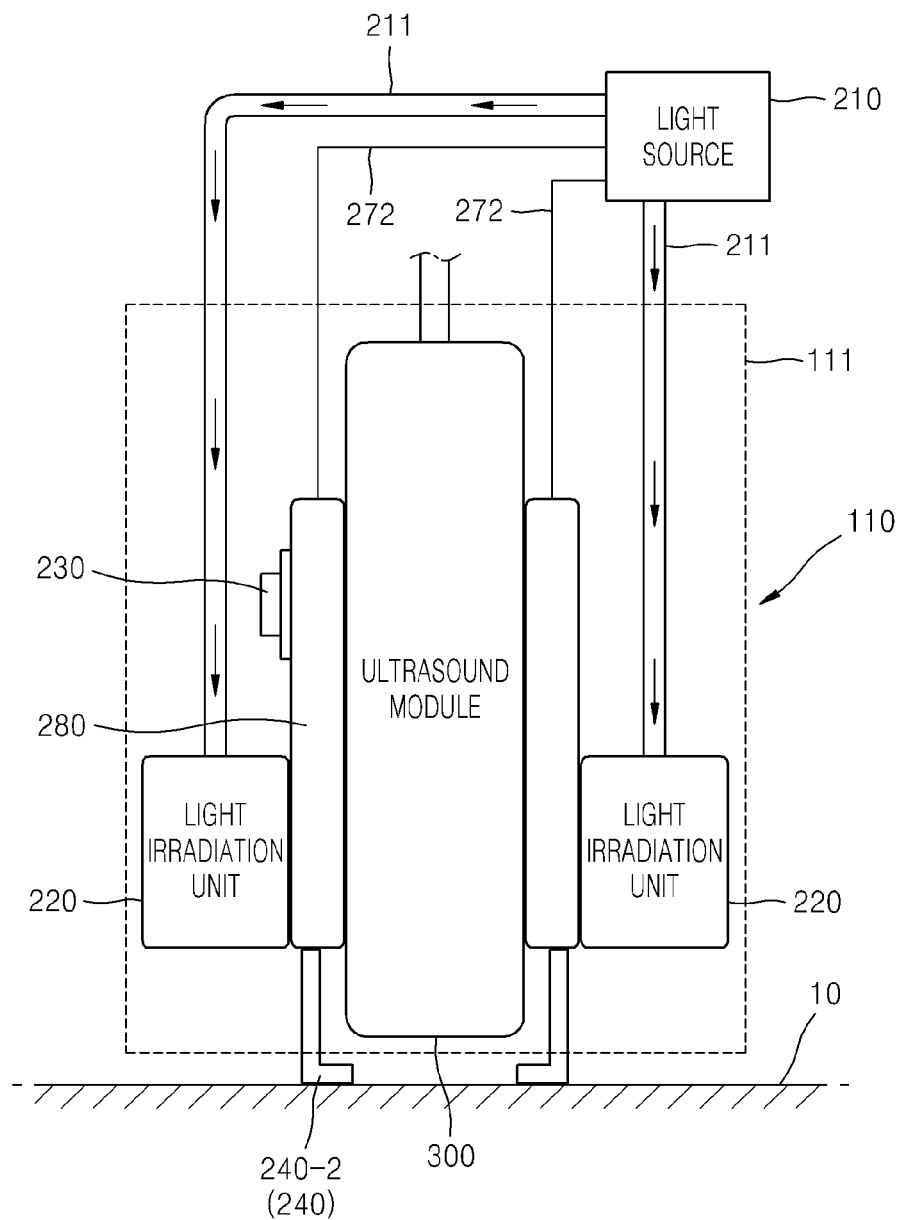
FIG. 5 is a view schematically illustrating a photoacoustic probe according to an embodiment of the present invention.

FIG. 5 is a view schematically illustrating the photoacoustic probe 110 according to an embodiment of the present invention. As illustrated in FIG. 5, the ultrasound module 300 and the light irradiation unit 220 may be disposed inside a probe body 111. The light irradiation unit 220 may be disposed at a side portion of the ultrasound module 300. Two light irradiation units 220 may be disposed with the ultrasound module 300 as the center. However, it is not limited thereto, and the light irradiation unit 220 may be one, or three or more.

Light output from the light source 210 may be transmitted to the light irradiation unit 220 via a light transmission unit 211. The light transmission unit 211 may include at least one optical fiber.

The contact detection unit 240 protrudes over the probe body 111 and may be moved by being pressurized by a contact with the subject 10. For example, the contact detection unit 240 may move to a first location 240-1 protruding outwards from the probe body 111 and to a second location 240-2 inserted more inwards toward the photoacoustic probe than the first location.

The user input unit 230 receives an input signal from a user for the light irradiation unit 220 to irradiate light and may receive the input signal by pressurization by the user. The user input unit 230 may be formed in the probe body 111. For example, the user input unit 230 may be formed in a case 280 disposed between the light irradiation unit 220 and the ultrasound module 300.

Figure 6A:
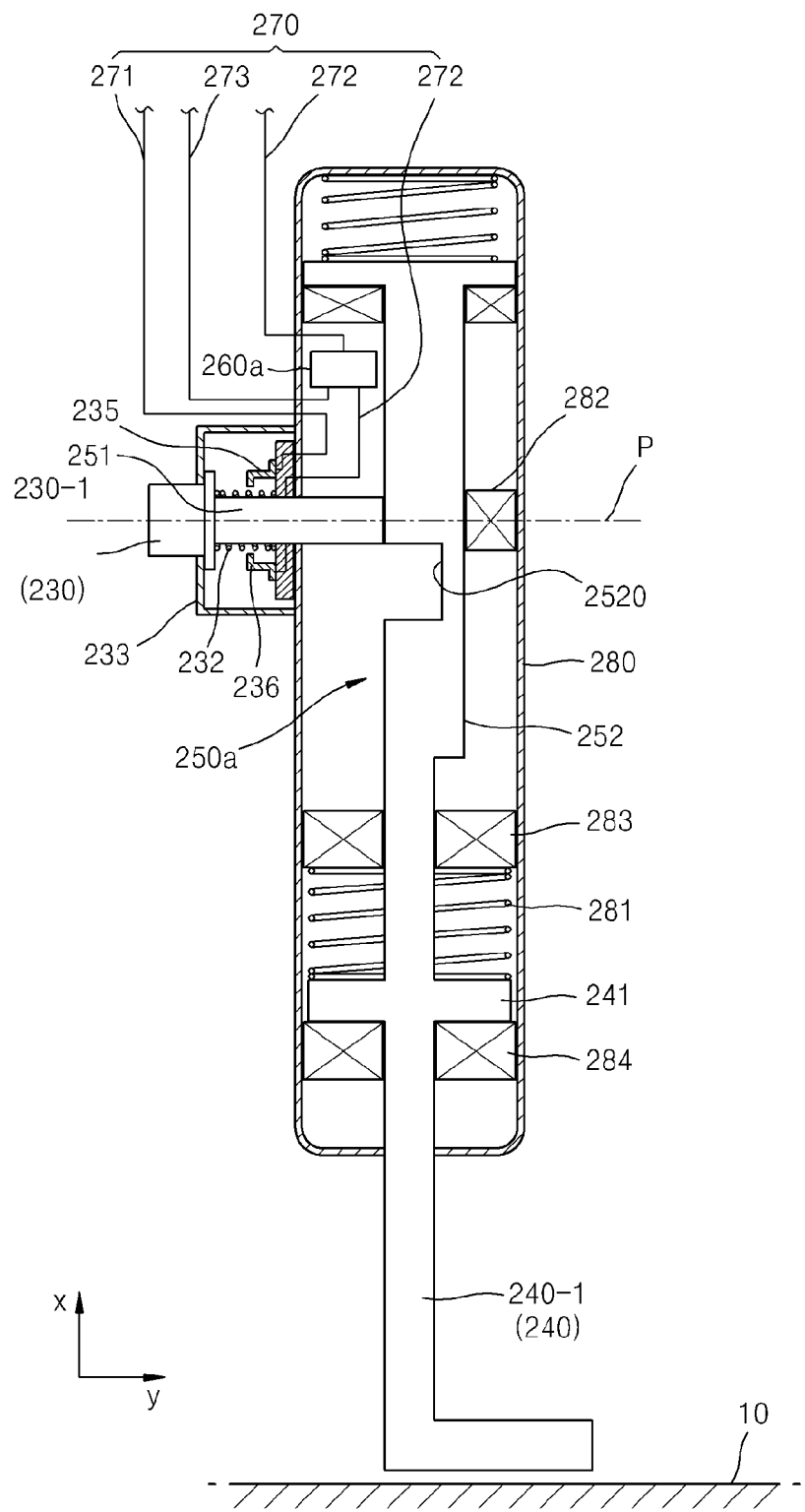
FIGS. 6A and 6B are views conceptually illustrating an embodiment in which a contact detection unit and a user input unit are formed in FIG. 5.
Figure 6B:
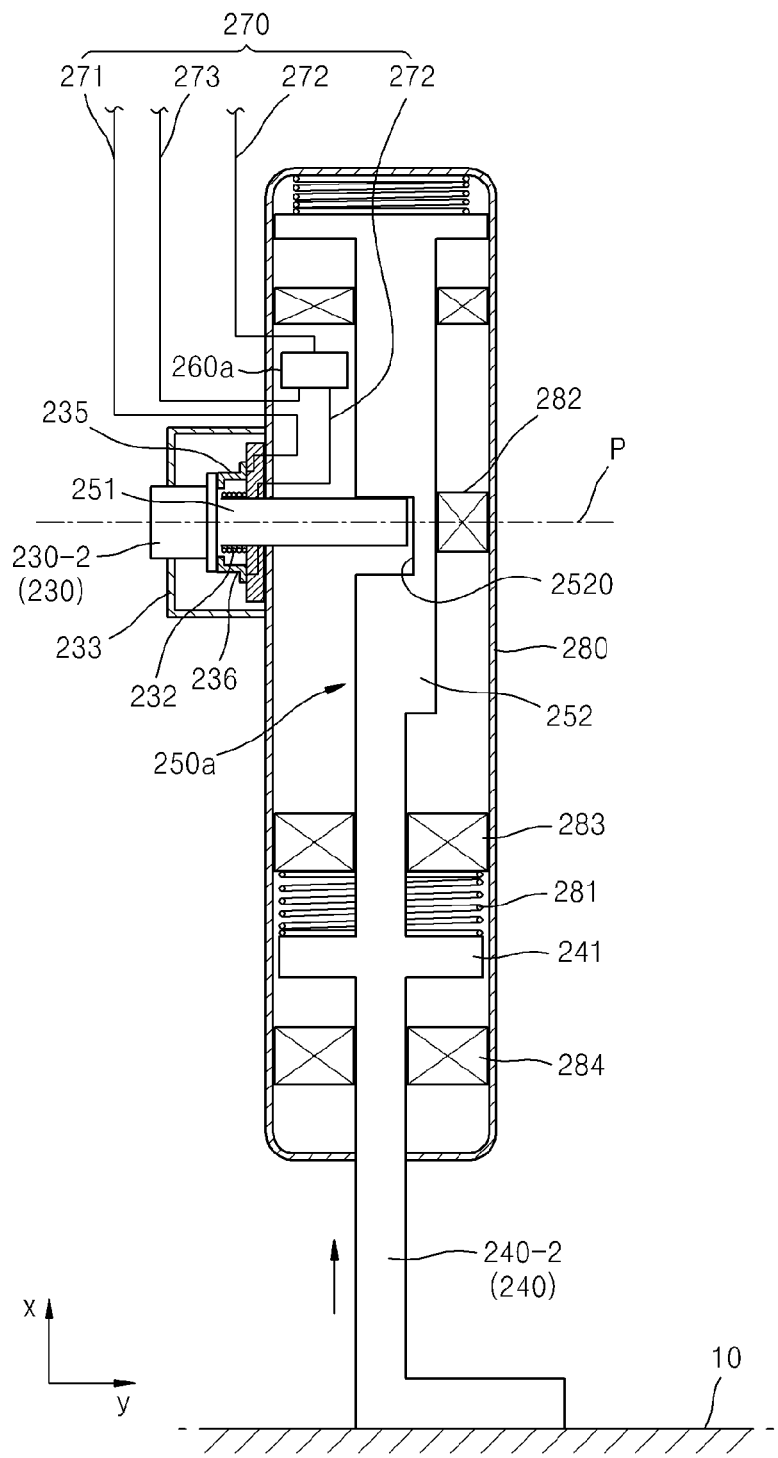

FIGS. 6A through 6B are views conceptually illustrating an embodiment in which the contact detection unit 240 and the user input unit 230 are formed in the situation of FIG. 5. FIG. 6A illustrates a situation in which the user input unit 230 is pressurized by a user in a state in which the contact detection unit 240 is located in the first location 240-1, and FIG. 6B illustrates a situation in which the user input unit 230 is pressurized by the user in a state in which the contact detection unit 240 is located in the second location 240-2.

When the contact detection unit 240 does not contact the subject 10, the contact detection unit 240 is located in the first location 240-1. In this case, the contact detection unit 240 is pressurized forwards by an elastic member 281 and remains to be in the first location 240-1 by a stopper 284.

When an end of the contact detection unit 240 contacts the subject 10 and the contact detection unit 240 is pressurized backwards by a greater force than a force applied by the elastic member 281, the contact detection unit 240 moves backwards and is located in the second location 240-2. Here, a forward direction is defined as a direction toward the subject 10, and a backward direction is defined as a direction opposite to the forward direction.

The contact detection unit 240 may move from the first location 240-1 to the second location 240-2 by a contact with the subject 10. When the contact detection unit 240 is released from the contact with the subject 10, the contact detection unit 240 may move from the second location 240-2 to the first location 240-1 by the elastic member 281. Like this, the contact detection unit 240 may move in a predetermined direction, for example, in a first direction x. The first direction x includes the above described forward or backward direction. A protrusion 241 of the contact detection unit 240 may be restricted from a movement by the stopper 284. Accordingly, the contact detection unit 240 may move within a predetermined section. Reference numeral 282 denotes a guide that supports a side surface of the contact detection unit 240 and guides a location movement of the contact detection unit 240, and reference numeral 283 denotes a supporting unit that supports the elastic member 281.

The user input unit 230 may move in a cross direction of the first direction x, for example, a perpendicular second direction y. The user input unit 230 is a means by which an input signal that emits light from the light source 210 is input, and the input signal may be received by pressurization. For example, the user input unit 230 may be a press button. The user input unit 230 may move from a third location 230-1 to a fourth location 230-2 by pressurization by the user. The third location 230-1 is a state in which the input signal is not received, and the fourth location 230-2 is a state in which the input signal is received. For example, when the user input unit 230 is in the third location 230-1, the user input unit 230 is in a state in which the user input unit 230 does not contact metal contact points 235 and 236 to receive the input signal, and when the user input unit 230 is in the fourth location 230-2, the user input unit 230 contacts the metal contact points 235 and 236. The metal contact point 235 is connected to a first input signal line 271 connected to an input signal generation unit (not shown) that generates an input signal, and the metal contact point 236 is connected to a second input signal line 272 connected to the light source 210.

When the user input unit 230 is located in the third location 230-1, the user input unit 230 and the metal contact points 235 and 236 do not contact each other, and thus, the first input signal line 271 and the second input signal line 272 are not connected to each other. When the user input unit 230 is located in the fourth location 230-2, the user input unit 230 contacts the metal contact points 235 and 236, and thus, the first input signal line 271 and the second input signal line 272 are connected to each other. The user input unit 230 may move from the third location 230-1 to the fourth location 230-2 by pressurization, and, when the pressurization by the user is released, the user input unit 230 may move from the fourth location 230-2 to the third location 230-1 by an elastic member 232. A case 233 protects the metal contact points 235 and 236 and the elastic member 232, and prevents the user input unit 230 from protruding by more than a predetermined distance.

As shown above, when the user input unit 230 is located in the third location 230-1, the input signal generated in the input signal generation unit may not be transmitted to the second input signal line 272, and, when the user input unit 230 is located in the fourth location 230-2, the input signal generated in the input signal generation unit may be transmitted to the second input signal line 272 through the first input signal line 271 and the user input unit 230. Here, the meaning of receiving the input signal includes not only transmitting the input signal generated in the signal generation unit to a direction of the light source 210, but also generating the input signal in the user input unit 230. Meanwhile, the above described embodiments are described based on the example in which the user input unit 230 protrudes more when the user input unit 230 is in the third location 230-1 than when the user input unit 230 is in the fourth location 230-2. However, it is not limited thereto, and, according to situations, the user input unit 230 may protrude more when the user input unit 230 is in the fourth location 230-2 than when the user input unit 230 is in the third location 230-1.

The movement restriction unit 250a is disposed between the contact detection unit 240 and the user input unit 230. The movement restriction unit 250a selectively restricts the location movement of the user input unit 230 based on the location of the contact detection unit 240. For example, the movement restriction unit 250a restricts the location movement of the user input unit 230 when the contact detection unit 240 is located in the first location 240-1, and permits the location movement of the user input unit 230 when the contact detection unit 240 is located in the second location 240-2. By this, when the contact detection unit 240 does not contact the subject 10, the location movement of the user input unit 230 is restricted even when the user input unit 230 is pressurized, and thus, unintentional light irradiation by the light irradiation unit 220 may be prevented.

The movement restriction unit 250a includes a first connection rod 251, and a second connection rod 252 in which an insertion portion 2520 into which an end of the first connection rod 251 may be inserted is formed. The first connection rod 251 is connected to the user input unit 230, and the second connection rod 252 is connected to the contact detection unit 240.

For example, an end of the first connection rod 251 may be fixed to the user input unit 230. Accordingly, the first connection rod 251 may move in connection with the movement of the user input unit 230. The second connection rod 252 may be fixed to the contact detection unit 240. For example, the second connection rod 252 may be integrally formed with the contact detection unit 240. Accordingly, the second connection rod 252 may move in connection with the movement of the contact detection unit 240.

A movement direction y of the first connection rod 251 and a movement direction x of the second connection rod 252 may cross each other. For example, the first connection rod 251 may move in the direction y perpendicular to the movement direction x of the second connection rod 252.

Referring to FIG. 6A, when the contact detection unit 240 is located in the first location 240-1, the insertion portion 2520 is located outside a movement path P of the first connection rod 251. Accordingly, the end of the first connection rod 251 is restricted from being inserted into the insertion portion 2520. Thus, although the user pressurizes the user input unit 230, the user input unit 230 may not move to the fourth location 230-2 since the end of the first connection rod 251 may not be inserted into the insertion portion 2520. Therefore, even if the user pressurizes the user input unit 230, light is not irradiated by the light irradiation unit 220.

In contrast, referring to FIG. 6B, when the contact detection unit 240 is located in the second location 240-2, the insertion portion 2520 is located in the movement path P of the first connection rod 251. Accordingly, the end of the first connection rod 251 may be inserted into the insertion portion 2520. Thus, when the user pressurizes the user input unit 230, the user input unit 230 moves from the third location 230-1 to the fourth location 230-2 by the pressurization. In this case, the end of the first connection rod 251 is inserted to the insertion portion 2520 of the second connection rod 252.

The condition determination unit 260a may be disposed between the user input unit 230 and the light source 210 (refer to FIG. 5). The condition determination unit 260a may selectively connect between the user input unit 230 and the light source 210, based on an image measurement mode. The condition determination unit 260a selectively transmits an input signal transmitted from the user input unit 230 to the light source 210 based on information about the image measurement mode provided through an image signal line 273. For this, the condition determination unit 260a may include a logic gate, a microprocessor, etc. The image signal line 273 may be connected to the control unit 160 (refer to FIG. 4).

When the image measurement mode is not a photoacoustic image measurement mode, for example, when the image measurement mode is an ultrasound image measurement mode or when there is no input with respect to the image measurement mode, the condition determination unit 260a does not transmit the input signal transmitted from the user input unit 230 to the light source 210. That is, even if the user input unit 230 is located in the fourth location 230-2, light may be prevented from being incident from the light source 210, when the image measurement mode is not the photoacoustic image measurement mode.

Figure 7A:
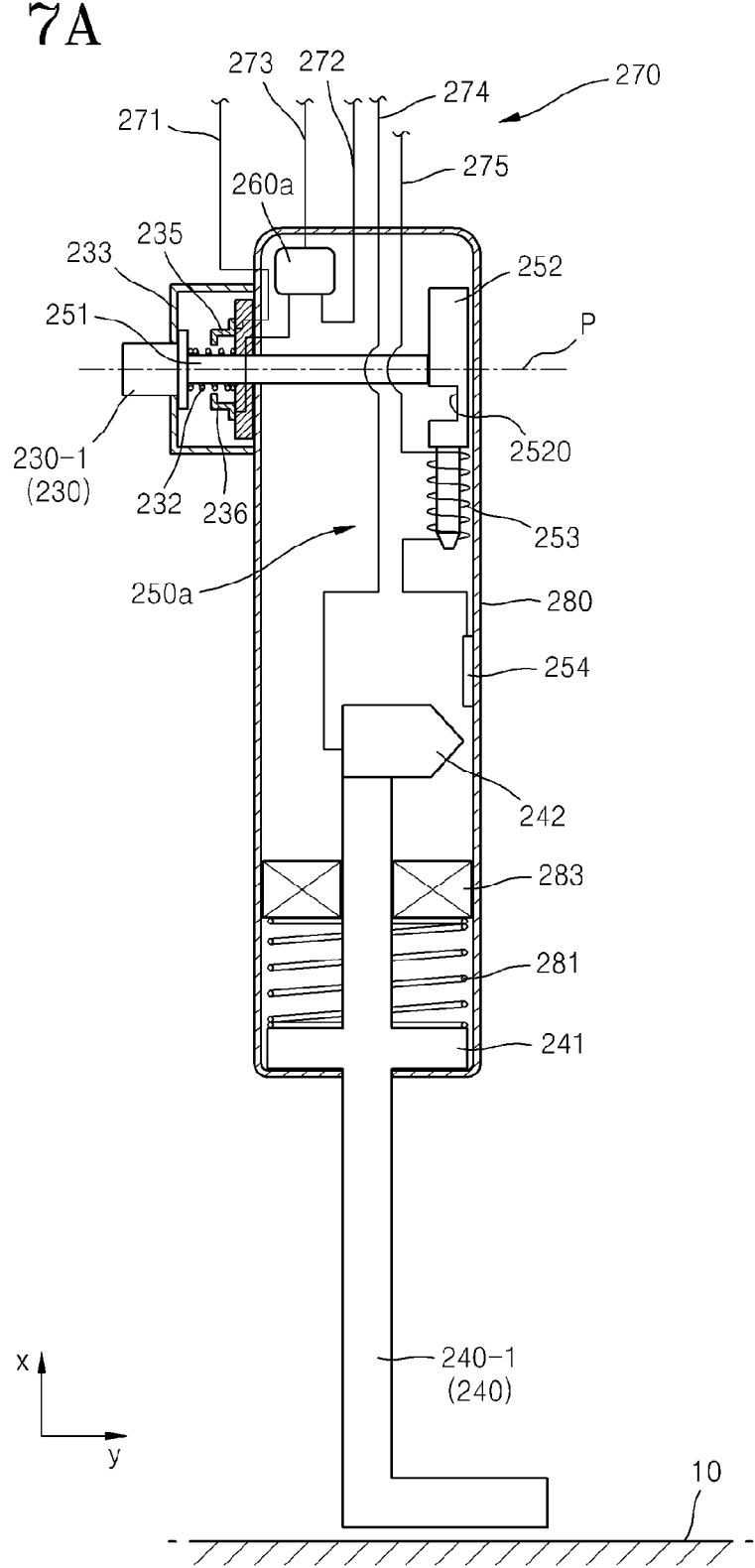
FIGS. 7A and 7B are views conceptually illustrating another embodiment in which a contact detection unit and a user input unit are formed in FIG. 5.
Figure 7B:
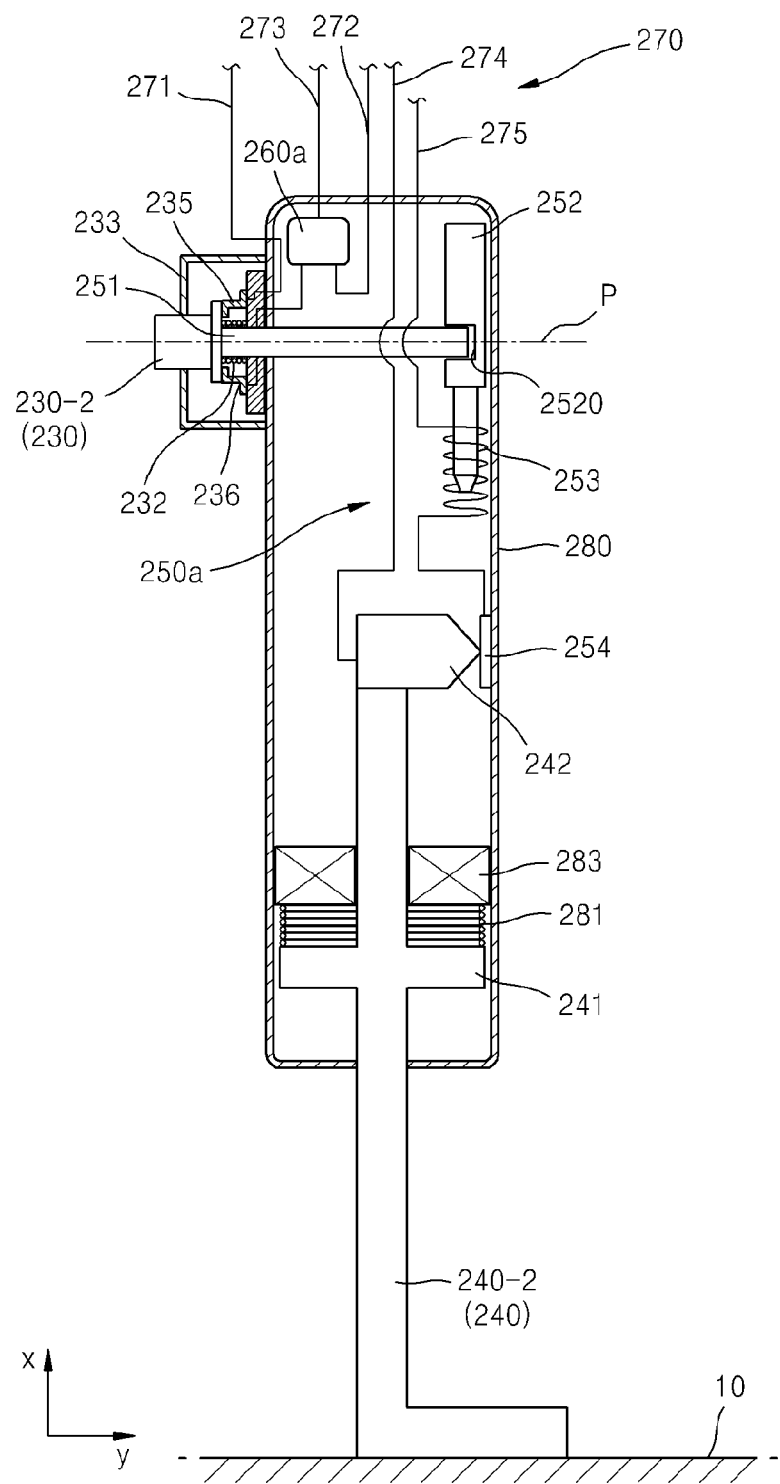

FIGS. 7A through 7B are views conceptually illustrating another embodiment in which the contact detection unit 240 and the user input unit 230 are formed in the situation of FIG. 5. FIG. 7A illustrates a situation in which the user input unit 230 is pressurized by a user in a state in which the contact detection unit 240 is located in the first location 240-1. FIG. 7B illustrates a situation in which the user input unit 230 is pressurized by the user in a state in which the contact detection unit 240 is located in the second location 240-2. Hereinafter, descriptions of identical aspects with aspects described by referring to FIGS. 6A and 6B will be omitted and only different aspects will be described.

Referring to FIGS. 7A and 7B, the movement restriction unit 250a includes the first connection rod 251, the second connection rod 252, and a driving unit 253.

The first connection rod 251 is fixed to the user input unit 230. The second connection rod 252 is not fixed to the contact detection unit 240 unlike the case of FIGS. 6A and 6B. The second connection rod moves in a cross direction of the movement direction of the first connection rod 251 by the driving unit 253.

The driving unit 253 is disposed between the second connection rod 252 and the contact detection unit 240. The driving unit 253 performs a function that moves the second connection rod 252 in a cross direction of the movement direction of the first connection rod 251. The driving unit 253 may include a solenoid that moves the second connection rod 252 in a straight line. However, the driving unit 253 is not limited to the solenoid, and various driving devices for a straight movement may be used. In addition, the driving unit 253 is not limited to a way of moving the second connection rod 252 in a straight line, and various movement ways may be employed. For example, driving devices that employ a wobbling movement or a rotation movement may be used.

The driving unit 253 is selectively connected with the contact detection unit 240 based on a location movement of the contact detection unit 240. A first electrical contact unit 242 is formed in the contact detection unit 240, and a second electrical contact unit 254 is formed in the driving unit 253. The first electrical contact unit 242 is connected to a first driving signal line 274 that transmits the driving signal. The second electrical contact unit 254 is formed at an end of the driving unit 253, and the other end of the driving unit 253 may be connected to a second driving signal line 275. The first driving signal line 274 and the second driving signal line 275 may be connected to a driving signal generation unit (not shown) that generates a driving signal.

As the contact detection unit 240 moves from the first location 240-1 to the second location 240-2, the first electrical contact unit 242 of the contact detection unit 240 contacts the second electrical contact unit 254 of the driving unit 253. The first electrical contact unit 242 may have a shape in which a portion of the first electrical contact unit 242 that contacts the second electrical contact unit 254 is sloped. By this, the first electrical contact unit 242 may stably contact the second electrical contact unit 254 in a process of the location movement.

As the contact detection unit 240 moves from the second location 240-2 to the first location 240-1, the first electrical contact unit 242 of the contact detection unit 240 is released from the contact with the second electrical contact unit 254 of the driving unit 253.

Referring to FIG. 7A, when the contact detection unit 240 is located in the first location 240-1, the first electrical contact unit 242 and the second electrical contact unit 254 are not connected to each other. Accordingly, a driving signal is not transmitted to the driving unit 253, and the insertion portion 2520 of the second connection rod 252 remains to be outside the movement path P of the first connection rod 251. Thus, even if the user pressurizes the user input unit 230, the light irradiation unit 220 may not irradiate light since the user input unit 230 is incapable of moving to the fourth location 230-2.

Referring to FIG. 7B, when the contact detection unit 240 is located in the second location 240-2, the first electrical contact unit 242 and the second electrical contact unit 254 are connected to each other. Accordingly, a driving signal is transmitted to the driving unit 253 so that the second connection rod 252 moves in a cross direction of the movement direction of the first connection rod 251. As the second connection rod 252 moves, the insertion portion 2520 of the second connection rod 252 is located in the movement path P of the first connection rod 251. Thus, when the user pressurizes the user input unit 230, an end of the first connection rod 251 connected to the user input unit 230 is inserted into the insertion portion 2520, and the user input unit 230 is located in the fourth location 230-2.

Even if the user input unit 230 is located in the fourth location 230-2, light may be prevented from being incident from the light source 210 when the image measurement mode is not the photoacoustic image measurement mode, by the condition determination unit 260a disposed between the user input unit 230 and the light source 210.

Figure 8:
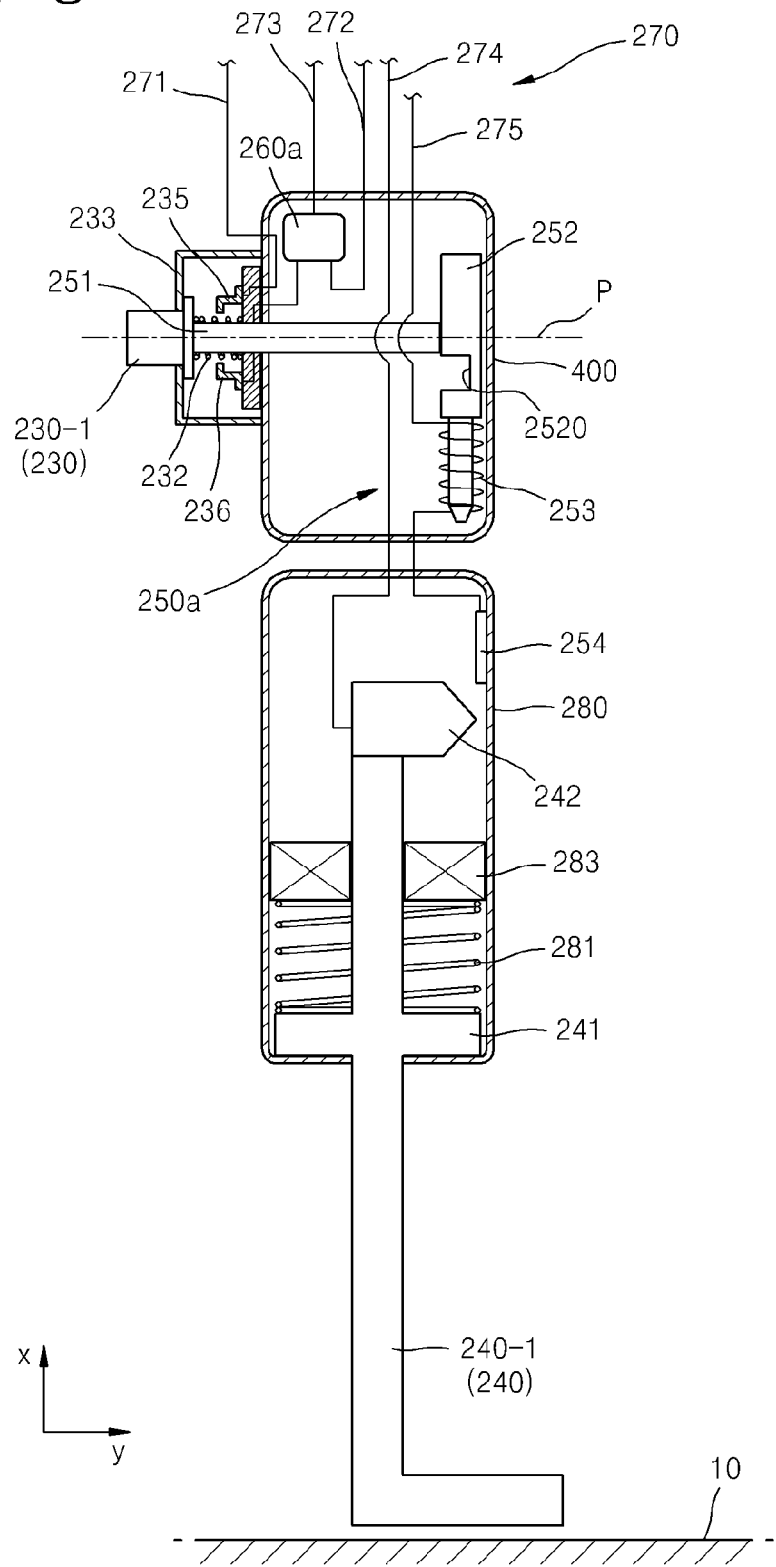
FIG. 8 is a variation embodiment of FIG. 7A.

As shown above, the location of the user input unit 230 may be freely formed by including the driving unit 253. For example, there is no need to design such that the user input unit 230 is disposed adjacent to the contact detection unit 240, or the location movement of the user input unit 230 is performed in a cross direction of the movement direction of the contact detection unit 240. Accordingly, the user input unit 230 may be included in the photoacoustic diagnostic apparatus 400 provided separately from the case 280 including the contact detection unit 240, as illustrated in FIG. 8. The device 400 may be a control panel of a main body or a part of the main body, or may be a foot switch.

Figure 9A:
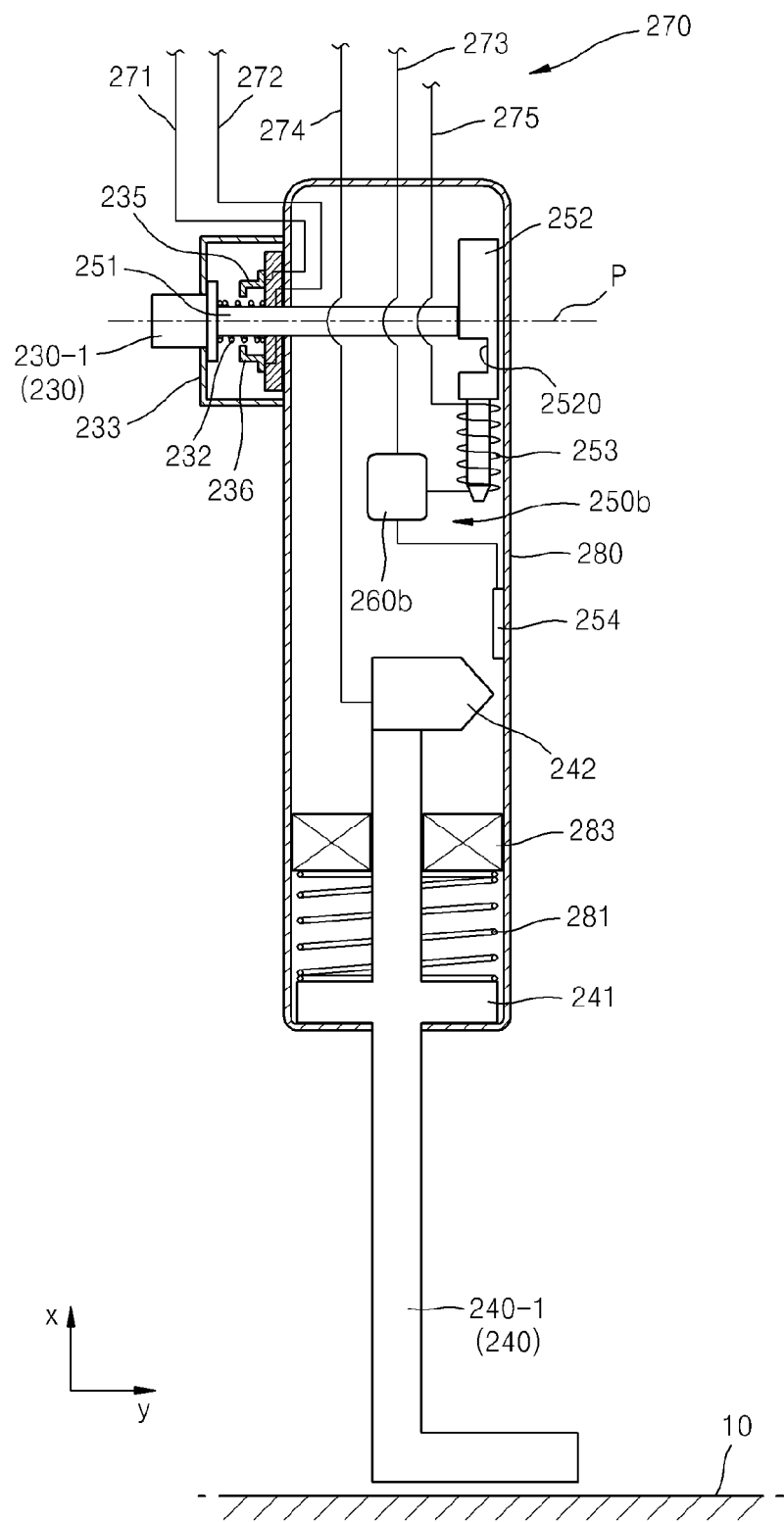
FIGS. 9A through 9C are views conceptually illustrating another example in which a contact detection unit and a user input unit are formed.
Figure 9B:
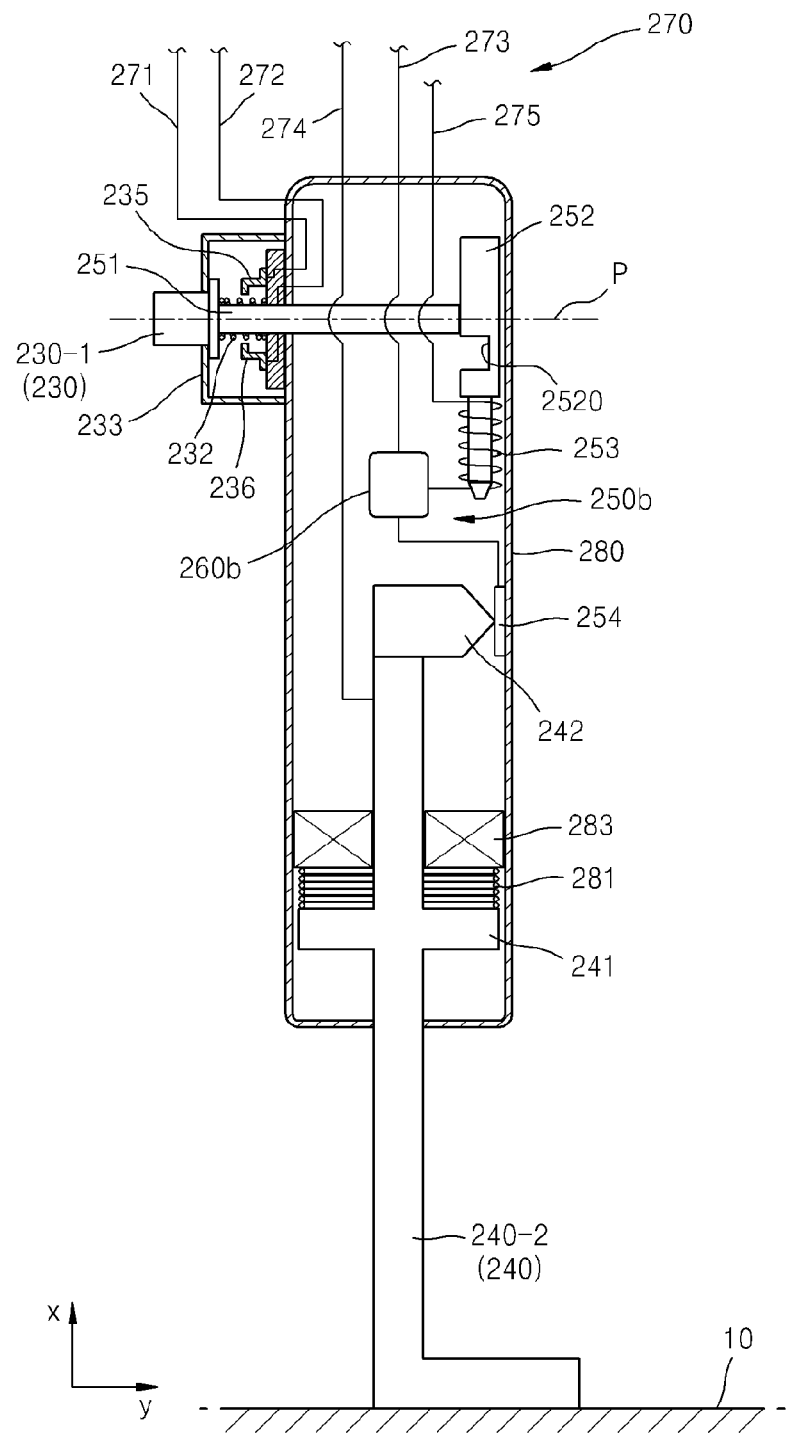
Figure 9C:
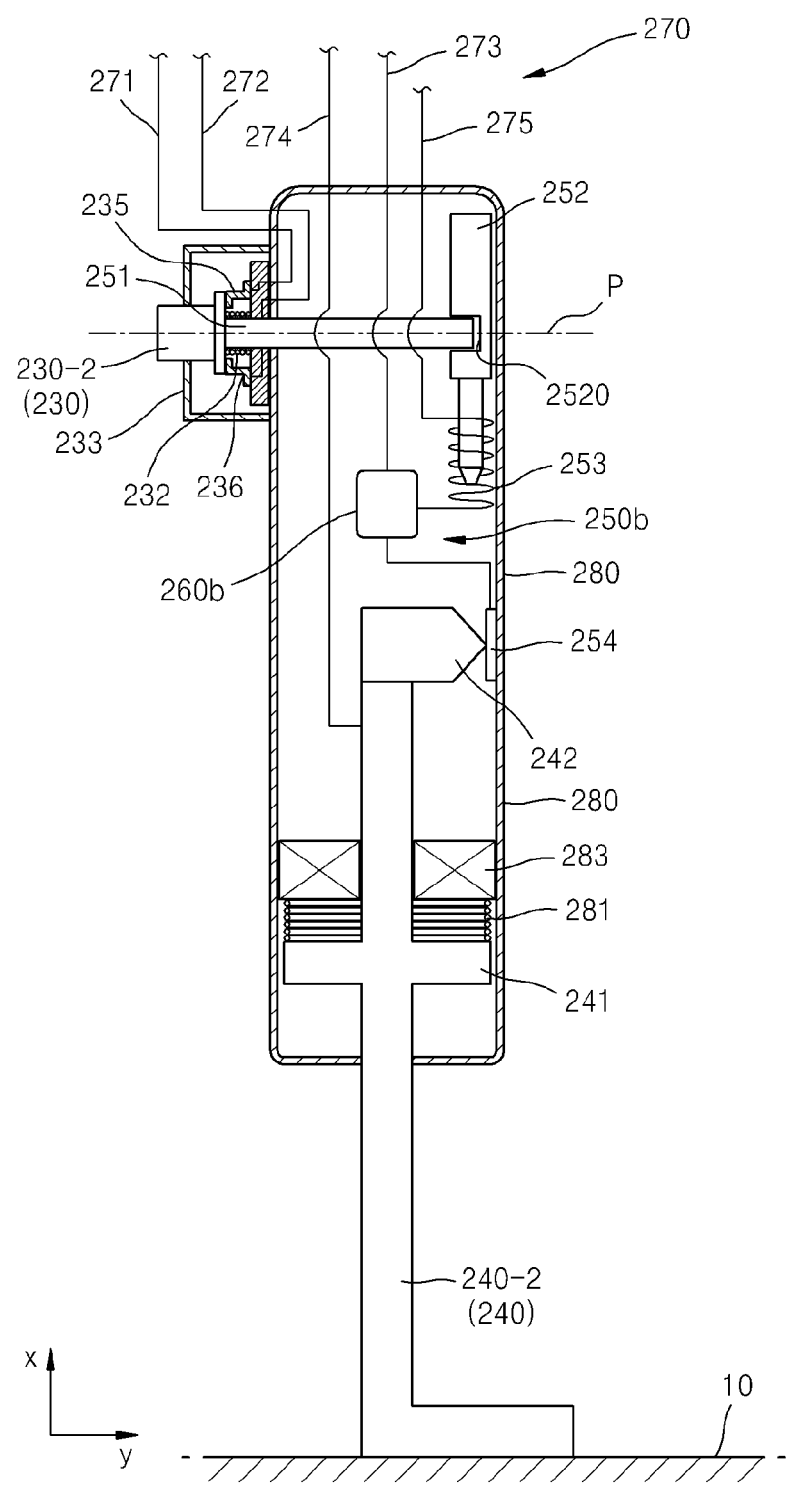

FIGS. 9A through 9C are views conceptually illustrating another example in which the contact detection unit 240 and the user input unit 230 are formed. FIG. 9A illustrates a case in which the user input unit 230 is pressurized when the contact detection unit 240 is located in the first location 240-1, FIG. 9B illustrates a case in which the user input unit 230 is pressurized when the contact detection unit 240 is located in the second location 240-2 and the image measurement mode is an ultrasound image measurement mode, and FIG. 9C illustrates a case in which the user input unit 230 is pressurized when the contact detection unit 240 is located in the second location 240-2 and the image measurement mode is a photoacoustic image measurement mode. Hereinafter, descriptions of identical aspects with the aspects described by referring to FIGS. 7A and 7B will be omitted and only different aspects will be described.

The condition determination unit 260b may be disposed between the contact detection unit 240 and the user input unit 230. For example, the condition determination unit 260b may be included in the movement restriction unit 250b disposed between the contact detection unit 240 and the user input unit 230.

The movement restriction unit 250b includes the first connection rod 251, the second connection rod 252, the driving unit 253, and the condition determination unit 260b. An operation relationship of the first connection rod 251, the second connection rod 252, and the driving unit 253 are similar to the above described embodiments, and thus, its detailed descriptions will be omitted.

The condition determination unit 260b may be disposed between the driving unit 253 and the contact detection unit 240. The condition determination unit 260b performs a function that selectively transmits a driving signal to the driving unit 253, when a first electrical contact unit 242 of the contact detection unit 240 contacts the second electrical contact unit 254. The condition determination unit 260b transmits the driving signal to the driving unit 253 when the image measurement mode is a photoacoustic image measurement mode, but does not transmit the driving signal to the driving unit 253 when the image measurement mode is not the photoacoustic image measurement mode.

Referring to FIG. 9A, when the contact detection unit 240 is located in the first location 240-1, the first electrical contact unit 242 and the second electrical contact unit 254 are not connected to each other. Accordingly, a driving signal is not transmitted to the driving unit 253 and the insertion portion 2520 of the second connection rod 252 remains to be outside the movement path P of the first connection rod 251. Thus, even if the user pressurizes the user input unit 230, light may not be irradiated by the light irradiation unit 220 since the user input unit 230 is incapable of moving to the fourth location 230-2.

Referring to FIG. 9B, when the contact detection unit 240 is located in the second location 240-2, the first electrical contact unit 242 and the second electrical contact unit 254 are connected to each other. Accordingly, the driving signal is transmitted to the condition determination unit 260b by passing through the first electrical contact unit 242 and the second electrical contact unit 254. When the image measurement mode is not the photoacoustic image measurement mode, the condition determination unit 260b does not transmit the driving signal to the driving unit 253. Accordingly, the second connection rod 252 does not move and remains to be outside the movement path P of the first connection rod 251. Thus, even if the contact detection unit 240 is located in the second location 240-2 and the user pressurizes the user input unit 230, light may not be irradiated by the light irradiation unit 220 since the user input unit 230 is incapable of moving to the fourth location 230-2.

FIG. 9C illustrates a case in which the image measurement mode is the photoacoustic image measurement mode. When the contact detection unit 240 is located in the second location 240-2, the first electrical contact unit 242 and the second electrical contact unit 254 are connected to each other and the driving signal is transmitted to the condition determination unit 260b. Since the image measurement mode is the photoacoustic image measurement mode, the condition determination unit 260b transmits the driving signal to the driving unit 253. The second connection rod 252 moves in a cross direction of the movement direction of the first connection rod 251 by the driving unit 253. As the second connection rod 252 moves, the insertion portion 2520 of the second connection rod 252 is located in the movement path P of the first connection rod 251. Thus, when the user pressurizes the user input unit 230, an end of the first connection rod 251 connected to the user input unit is inserted into the insertion portion 2520, and the user input unit 230 is located in the fourth location 230-2. Light may be irradiated by the light irradiation unit 220.

As shown above, only when the two conditions, that is, the location of the contact detection unit 240 and whether the image measurement mode is the photoacoustic image measurement mode, are met, light irradiation is permitted by enabling a movement of the user input unit 230. When any of these two conditions are not met, light irradiation due to an unintentional movement of the user input unit 230 may be more stably prevented.

As described above, according to the one or more of the above embodiments of the present invention, the photoacoustic probe and the photoacoustic diagnostic apparatus may prevent laser irradiation from the photoacoustic diagnostic apparatus even when a person performing a diagnosis manipulates the user input unit through his/her carelessness. Therefore, damage to a human body due to the unintentional laser irradiation may be prevented.

The particular implementations shown and described herein are illustrative examples of the invention and are not intended to otherwise limit the scope of the invention in any way. For the sake of brevity, conventional electronics, control systems, software development and other functional aspects of the systems (and components of the individual operating components of the systems) may not be described in detail. Furthermore, the connecting lines, or connectors shown in the various figures presented are intended to represent exemplary functional relationships and/or physical or logical couplings between the various elements. It should be noted that many alternative or additional functional relationships, physical connections or logical connections may be present in a practical device. Moreover, no item or component is essential to the practice of the invention unless the element is specifically described as "essential" or "critical".

It should be understood that the exemplary embodiments described herein should be considered in a descriptive sense only and not for purposes of limitation. Descriptions of features or aspects within each embodiment should typically be considered as available for other similar features or aspects in other embodiments.

While one or more embodiments of the present invention have been described with reference to the figures, it will be understood by those of ordinary skill in the art that various changes in form and details may be made therein without departing from the spirit and scope of the present invention as defined by the following claims.

What is claimed is:
1. A photoacoustic diagnostic apparatus comprising:
a photoacoustic probe comprising a light irradiation unit that irradiates light to a subject and a transducer that receives ultrasound generated from the subject and converts the ultrasound into an electric signal;

a moving member that is configured to move between a first location and a second location, wherein the first location is farther away from the user input than the second location;

a user input that receives an input signal from a user for the light irradiation unit to irradiate light and is configured to move between a third location in which receipt of the input signal is disabled and a fourth location in which the receipt of the input signal is enabled; and a movement restraint that selectively restricts movement of the user input based on the location of the moving member, the movement restraint comprises a first connection rod connected to the user input and a second connection rod which is connected to the moving member and which includes a recess to into which at least a portion of the first connection rod can be inserted, wherein the first connection rod is configured to move in connection with the movement of the user input and the second connection rod is configured to move in connection with the movement of the moving member.

2. The photoacoustic diagnostic apparatus of claim 1, wherein the user input is restricted from moving from the third location to the fourth location by a location change of the moving member to the first location.

3. The photoacoustic diagnostic apparatus of claim 1, wherein the user input is configured to move from the third location to the fourth location by a location change of the moving member to the second location.

4. The photoacoustic diagnostic apparatus of claim 1, wherein the first connection rod is configured to move in a first direction, and the second connection rod is configured to move in a second direction which crosses the first direction.

5. The photoacoustic diagnostic apparatus of claim 1, wherein the first connection rod is fixed to the user input.

6. The photoacoustic diagnostic apparatus of claim 1, wherein the second connection rod is fixed to the moving member.

7. The photoacoustic diagnostic apparatus of claim 1, further comprising a processor that is provided between the user input and the light irradiation unit and upon determining that an image measurement mode is a photoacoustic image measurement mode, selectively connects between the user input and the light irradiation unit.

8. The photoacoustic diagnostic apparatus of claim 1, wherein the movement restraint further comprises a driving unit that moves the second connection rod.

9. The photoacoustic diagnostic apparatus of claim 8, wherein the driving unit selectively moves the second connection rod based on the location of the moving member.

10. The photoacoustic diagnostic apparatus of claim 8, further comprising a processor that is provided between the driving unit and the moving member,
wherein, upon determining that an image measurement mode is a photoacoustic image measurement mode, the processor selectively connects between the driving unit and the moving member.

11. The photoacoustic diagnostic apparatus of claim 1, wherein the moving member is disposed in the photoacoustic probe.

12. A photoacoustic probe comprising:
a probe body;
a light irradiation unit that is disposed inside the probe body and irradiates light to a subject;
a transducer that is disposed inside the probe body and receives ultrasound generated from the subject and converts the ultrasound into an electric signal;
a moving member that is configured to move between a first location and a second location, wherein the first location is farther away from the user input than the second location;
a user input that receives an input signal from a user for the light irradiation unit to irradiate light and is configured to move between a third location in which receipt of the input signal is disabled and a fourth location in which the receipt of the input signal is enabled; and
a movement restraint that selectively restricts a movement of the user input based on the location of the moving member, the movement restraint comprises a first connection rod connected to the user input and a second connection rod which is connected to the moving member and which includes a recess to into which at least a portion of the first connection rod can be inserted,
wherein the first connection rod is configured to move in connection with the movement of the user input and the second connection rod is configured to move in connection with the movement of the moving member.

13. The photoacoustic probe of claim 12, wherein the user input is restricted from moving from the third location to the fourth location by a location change of the moving member to the first location.

14. The photoacoustic probe of claim 12, wherein the user input is configured to move from the third location to the fourth location by a location change of the moving member to the second location.

* * * * *